United States Patent [19]
Liu et al.

[11] Patent Number: 5,492,988
[45] Date of Patent: Feb. 20, 1996

[54] HOMOGENEOUS POLYMERIZATION PROCESS FOR MAKING SUBSTANTIALLY HOMOGENEOUS TERPOLYMERS OF VINYL PYRROLIDONE, AN ORGANIC QUARTERNARY AMMONIUM MONOMER AND A HYDROPHOBIC MONOMER

[75] Inventors: Kou-Chang Liu, Wayne; Robert B. Login, Oakland; Yakir Reuven, West Orange, all of N.J.

[73] Assignee: ISP Investments Inc., Wilmington, Del.

[21] Appl. No.: 365,260

[22] Filed: Dec. 28, 1994

[51] Int. Cl.$^6$ .................. C08F 226/06; C08F 220/54; C08F 220/10
[52] U.S. Cl. .................. 526/264; 526/310; 526/328.5
[58] Field of Search .................. 526/264, 310, 526/328.5

[56] References Cited

U.S. PATENT DOCUMENTS

| | | | |
|---|---|---|---|
| 3,910,862 | 10/1975 | Barabas et al. | 526/264 |
| 4,039,734 | 8/1977 | Hendy | 526/258 |
| 4,521,404 | 6/1985 | Lorenz et al. | 526/264 |

Primary Examiner—Joseph L. Schofer
Assistant Examiner—Wu C. Cheng
Attorney, Agent, or Firm—Walter Katz; Marilyn J. Maue; Joshua J. Ward

[57] ABSTRACT

A homogeneous polymerization process is described for making substantially homogeneous terpolymers of, by weight, 55–99%, preferably 65–95% of vinyl pyrrolidone; 0.5–49%, preferably 1–25% of a quaternary amino monomer, preferably 3-methacrylamidopropyl trimethylammonium chloride; and 0.5–49%, preferably 1–25%, of a hydrophobic monomer, preferably octadecyl methacrylate. The homogeneous terpolymer provides dual hair styling and conditioning functions in hair care applications.

13 Claims, 2 Drawing Sheets

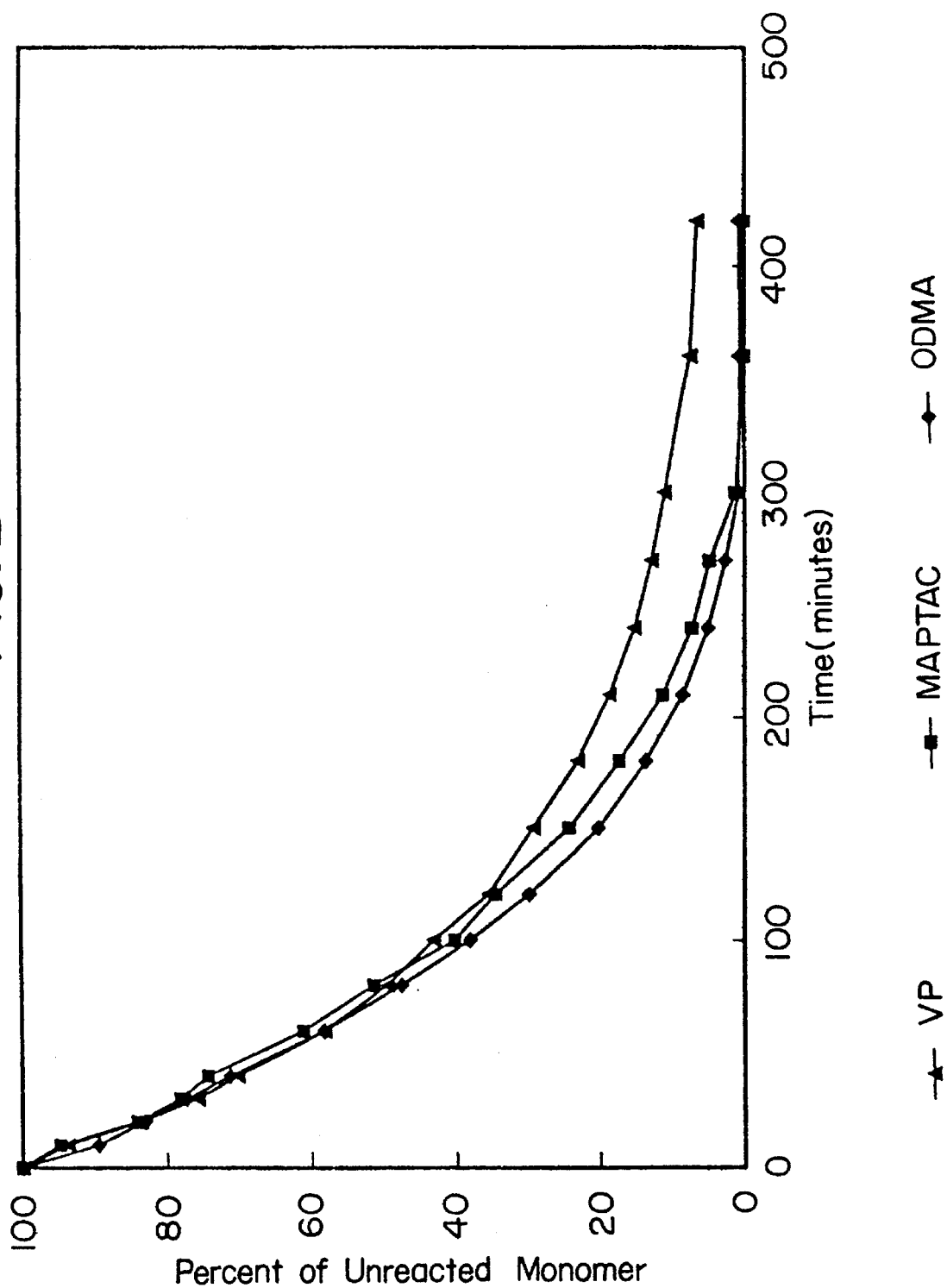

HOMOGENEOUS POLYMERIZATION PROCESS FOR MAKING SUBSTANTIALLY HOMOGENEOUS TERPOLYMERS OF VINYL PYRROLIDONE, AN ORGANIC QUARTERNARY AMMONIUM MONOMER AND A HYDROPHOBIC MONOMER

BACKGROUND OF THE INVENTION

1. Field of the Invention

This invention relates to a process for making substantially homogeneous terpolymers of vinyl pyrrolidone, a quaternary amino monomer and a hydrophobic monomer, for use in hair care applications.

2. Description of the Prior Art

Several synthetic polymers containing vinyl lactams are presently being used in cosmetic formulations, particularly in hair care products, to contribute body, set retention and conditioning to such products.

Representative of the art in this field are the following U.S. Pat. Nos. 3,914,403; 3,954,960; 4,057,533; 4,210,161; 4,586,518; 4,753,793; 4,764,363; 4,834,968; 4,842,850; 4,902,499; 4,906,459; 4,923,694; 4,963,348; 4,983,377; 5,011,895 and 5,015,708; and WO 91/15186; WO 91/15185; EPO 0412704A2; EPO 0412707A1; and JP 57126409.

These synthetic polymers generally are made by a "one-pot" polymerization process in which selected amounts of the several monomers are reacted together. The composition of the thus-formed polymer is considered as being the same as the composition of the charged monomers. However, such conventional non-homogeneous polymerization processes can provide only a mixture of polymers of various compositions, and, additionally, an indeterminate amount of homopolymers and undesired copolymers.

Accordingly, it is an object of this invention to provide a homogeneous polymerization process for making substantially homogeneous copolymers of vinyl pyrrolidone, a quaternary amino monomer and a hydrophobic monomer.

Another object of this invention is to provide a clear, aqueous solution of substantially homogeneous terpolymers of vinyl pyrrolidone (VP), 3-methacrylamidopropyl trimethylammonium chloride (MAPTAC), and RMA where R is $C_4$–$C_{32}$, and MA is methacrylate, preferably octadecyl methacrylate (ODMA), in a compositional range, by weight, of 55–99% VP, 0.5–49% MAPTAC and 0.5–49% ODMA.

Still another object herein is to provide clear, aqueous solutions of substantially homogeneous terpolymers of VP, MAPTAC and RMA in a predetermined compositional range and at a selected solids level, which, upon formulation into hair styling and conditioning compositions, will provide enhanced water solubility, and improved fixative, conditioning, and hair holding properties for the user.

SUMMARY OF THE INVENTION

A homogeneous polymerization process is described for making substantially homogeneous terpolymers comprising, by weight, 55–99%, preferably 65–95% of vinyl pyrrolidone, 0.5–49%, preferably 1–25% of a quaternary amino monomer, preferably 3-methacrylamidopropyl trimethylammonium chloride; and 0.5–49%, preferably 1–25%, of a hydrophobic monomer, preferably RMA, where R is $C_4$–$C_{32}$ alkyl, and, most preferably, octadecyl methacrylate.

Such homogeneous terpolymers provide both hair styling and conditioning for the user. The homogeneous terpolymer solution herein also has better clarity, and provides hair care products with greater water solubility, and improved polymer adsorption onto hair, when compared to non-homogeneous copolymers of the same composition, or related existing commercial products.

The homogeneous polymerization process of the invention includes precharging VP, and solvent, and introducing the MAPTAC and ODMA monomers incrementally at rates corresponding to the rate of disappearance of VP, over a given period of time.

IN THE DRAWINGS

FIG. 1 is a graphical representation of a conventional non-homogeneous ("one-pot") polymerization process for making a terpolymer of vinylpyrrolidone (VP), 3-methacrylamidopropyl trimethylammonium chloride (MAPTAC), and octadecyl methacrylate (ODMA) monomers from precharged amounts of the monomers. The relative monomer content of each monomer remaining during the polymerization is plotted vs. time.

FIG. 2 is a graphical representation of the homogeneous process of the invention for making the same terpolymer.

DETAILED DESCRIPTION OF THE INVENTION

A. TERPOLYMER OF INVENTION

1. Hydrophilic Monomers (a) Lactam Monomer

Figure 1:
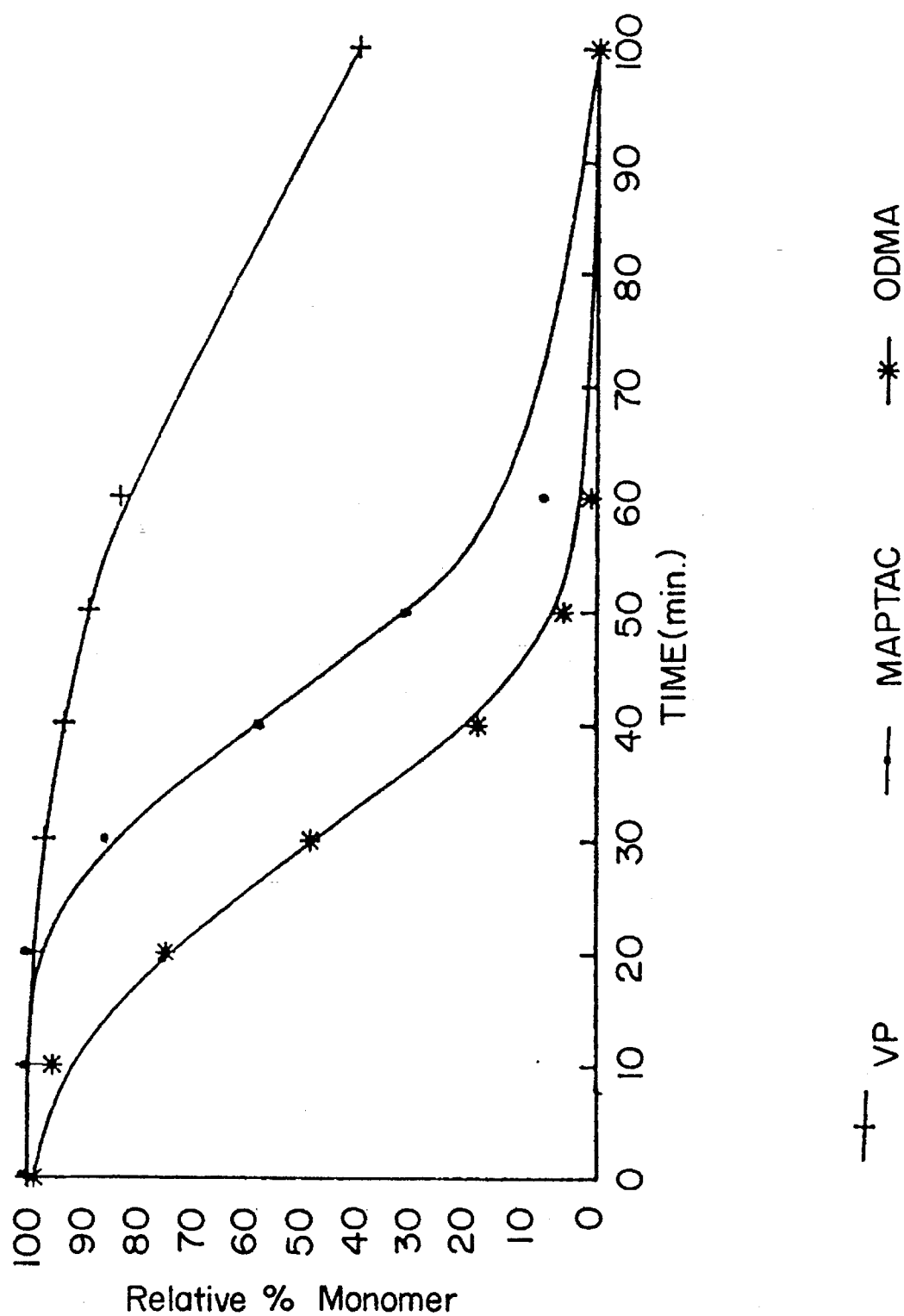

Vinylpyrrolidone is the most preferred vinyl lactam.

The vinyl lactam monomer is present in an amount of about 55–99%, and, preferably, 65–95%, by weight of the terpolymer.

(b) Quaternary Amino Acrylamide or Acrylate Monomer

The quaternary amino (or organic quaternary ammonium) acrylamide or acrylate monomer in the terpolymer of the invention has the formula:

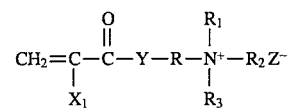

where

Y is O or —NX—;

R is $C_2$–$C_{20}$ alkyl or

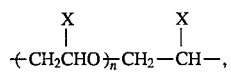

where n is 0–10,

X and $X_1$ are independently H, or $C_1$ to $C_8$ alkyl;

$R_1$, $R_2$ and $R_3$ are independently $C_1$–$C_4$ alkyl; and

Z is a halide, sulfate or sulfonate.

Suitable examples of amino acrylamides, acrylates, methacrylamides, or methacrylates which are employed as monomers in the terpolymer of the invention include quaternized salts of N-[12-(dimethylamino)dodecyl] methacrylamide or methacrylate;

N-[18-(dimethylamino)octadecyl] methacrylamide or methacrylate;

N-[8-(dimethyl-amino)octyl]methacrylamide or methacrylate;
N-[7-(dimethylamino)heptyl]acrylamide or acrylate;
N-[14-(dimethylamino)tetradecyl]acrylamide or acrylate;
N-[3-(dimethylamino)propyl]methacrylamide or methacrylate;
N-[3-(diethylamino)propyl]acrylamide or acrylate;
N-[4-(dipropylamino)butyl]methacrylamide or methacrylate;
N-[3-(methyl butyl amino)propyl]acrylamide or acrylate;
N-{2-[3-(dimethylamino)propyl]ethyl} acrylamide or acrylate; and
N-{4-[4-(diethylamino)butyl] butyl}acrylamide or acrylate.

Of the above group, the N-[(dimethylamino)alkyl]methacrylamides or acrylamides, methacrylates and acrylates of their quaternized halide, sulfate and sulfonate salts are preferred. Of these, 2-(ethyl dimethylammonium) ethyl methacrylate sulfate; (3-methacrylamidopropyl) trimethylammonium chloride (MAPTAC); (3-acrylamido-3-methylbutyl)propyl trimethylammonium bromide; (3-methacrylamido-3-ethylbutyl)propyl trimethylammonium chloride; (4-acrylamido-n-methylbutyl)propyl trimethylammonium chloride; and (3-methacrylamidopropyl) ethyl dimethylammonium ethyl sulfate, or a mixture thereof, are most preferred. Where the quaternized amino acrylamide is (3-methacrylamidopropyl)trimethylammonium chloride, the formula is represented by X and $X_1$ being $CH_3$; Y being NH; R being $C_3$ alkyl; $R_1$, $R_2$ and $R_3$ being methyl; and Z being chloride.

The quaternary amino monomer suitably is present in the terpolymer in an amount of about 0.5–49%, and, preferably 1–25%, by weight of the terpolymer.

The vinyl lactam and quaternary amino acrylamide or acrylate monomers constitute the hydrophilic portion of the terpolymer of the invention.

2. Hydrophobic Monomer

The hydrophobic monomer in the terpolymer of the invention suitably has the formula: RMA where R is a $C_4$–$C_{32}$ alkyl, preferably $C_{12}$–$C_{32}$ alkyl, or a mixture thereof; and MA is an acrylate, methacrylate, acrylamide or methacrylamide. Suitable hydrophobic monomers include 2-ethylhexyl methacrylate, dodecyl acrylate, tetradecyl acrylate, octadecyl methacrylate (ODMA), octadecyl methacrylamide, dodecyl acrylamide and 2-ethylhexyl methacrylamide. A preferred hydrophobic monomer is octadecyl methacrylate.

The hydrophobic monomer is present in an amount of about 0.5–49%, preferably 1–25%, by weight of the terpolymer.

B. HOMOGENEOUS POLYMERIZATION

The homogeneous polymerization process of the invention is illustrated by making substantially homogeneous terpolymers of VP, MAPTAC and ODMA in a predetermined composition.

In the homogeneous process, the least reactive monomer of the terpolymer (VP) is precharged into a reactor at a suitable reaction temperature, generally about 50°–80° C., and preferably 55°–75° C. The more reactive monomers (MAPTAC and ODMA) then are introduced incrementally into the VP-charged reactor at a rate which corresponds to the observed rate of disappearance of VP, over the period of polymerization.

The entire predetermined amount of the MAPTAC and ODMA monomers are added before substantially all the VP monomer has been consumed so that all monomers can react to form a substantially homogeneous terpolymer in a desired compositional ratio of VP:MAPTAC:ODMA. Consequently, a substantially homogeneous terpolymer is obtained whose composition approaches the nominal monomer ratio of the desired terpolymer composition and whose structure has the three individual monomeric units of the copolymer distributed substantially uniformly in a homogeneous chain along the backbone of the polymer.

The precharge in the process of the invention may include some MAPTAC and ODMA therein, generally in an amount of up to about 15% of the total amount of MAPTAC and ODMA required for a predetermined terpolymer composition without affecting the homogeneous polymerization process. However, it is still necessary that the rate of addition of MAPTAC and ODMA after any precharge be carried out at substantially the rate of disappearance of VP during polymerization.

The schedule of addition of MAPTAC and ODMA to accomplish the desired matched rate of reaction of VP is determined in the following manner.

DETERMINATION OF ADDITION SCHEDULES FOR MAPTAC AND ODMA TO FORM A HOMOGENEOUS TERPOLYMER WITH VP

A. First, a one-pot polymerization of VP, MAPTAC and ODMA monomers is carried out as follows:

EXAMPLE 1

VP (553.5 g), MAPTAC (124.5 g), ODMA (95.6 g) and ethanol (753.5 g) were charged into a 2-liter resin pot equipped with a gas inlet, a liquid inlet, a thermometer and a condenser. The pH of the solution was adjusted to about 7.5 with KOH. A stream of nitrogen then was bubbled through the solution during the reaction. The solution was gradually heated to 68° C. and 0.25 ml of Lupersol 11 as catalyst was added; then another 0.25 ml of the catalyst was added after 10 minutes; and another 6 units of 0.25 ml amount was added each 30 minutes. The reaction was carried out for an additional 3 hours.

The relative percentage amounts of residual monomers present during the course of the one-pot reaction was determined by gas chromatographic analysis after sampling the reaction mixture periodically. The analytical data obtained then was plotted as the graph of FIG. 1.

As shown in FIG. 1, the MAPTAC and ODMA monomers react much more rapidly than VP. Accordingly, after 100 minutes, for example, all the MAPTAC and ODMA monomers are consumed while residual VP monomer still is available for homopolymerization. Thus the terpolymer formed is of a composition different from the desired monomer ratios selected by the precharged amounts of the two monomers. Under these experimental conditions, the polymer product obtained is a complex mixture of a homopolymer which is polyvinylpyrrolidone, various copolymers, and a terpolymer of the several monomers of uncertain composition.

B. To form a homogeneous terpolymer, it is necessary that the curve of rate of reaction vs. time for both MAPTAC and ODMA substantially coincide or match the rate of reaction curve for VP. To accomplish this, the VP is precharged and substantially all the MAPTAC and RMA monomers are fed external to the precharge at a feeding schedule determined by analysis of the data of FIG. 1. The % MAPTAC and ODMA monomers to be fed at time t of the polymerization is determined from the Asymmetric Double Sigmoidal Distribution formula, $A_t$, below, which has four adjustable parameters, $a_1$, $a_2$, $a_3$ and $a_4$:

$$A_t = \frac{1}{1 + \exp\left[\dfrac{a_1 - \dfrac{a_2}{2} - t}{a_3}\right]} \left[1 - \frac{1}{1 + \exp\left[\dfrac{a_1 + \dfrac{a_2}{2} - t}{a_4}\right]}\right]$$

where t= time in minutes during copolymerization;

$a_1$ is a parameter which determines the center of the distribution;

$a_2$ is a parameter which affects the width of the distribution;

$a_3$ is a parameter which determines the ascending portion of the distribution; and $a_4$ is a parameter which determines the descending portion of the distribution.

$$\% \text{ MAPTAC or ODMA to be fed at time } t = \frac{A_t}{\sum_{t=0}^{N} A_T} \times 100$$

where

N=time when the polymerizations is completed.

To match the MAPTAC and ODMA curves to the VP curve of FIG. 1, an "initial guess" is made for the values of $a_1$, $a_2$, $a_3$ and $a_4$ for each of these monomers. Then these values are inserted into the $A_t$ formula and the % MAPTAC and ODMA to be fed at time t is calculated. The resulting % unreacted MAPTAC and ODMA during this polymerization will probably not match the % unreacted VP at the same time t. If the % unreacted MAPTAC or ODMA at time t is too large, then the value of $a_3$ (ascendency) in the $A_t$ formula is increased, $a_4$ (descendency) is decreased, $a_1$ (center) is decreased, and $a_2$ (width) is decreased. Conversely, if the initial guess values of $a_1$ through $a_4$ give a reaction rate for MAPTAC or ODMA which is too fast, then changes in the values of $a_1$ through $a_4$ are made in a direction opposite to those discussed above.

These new values of the parameters are then used to determine a new feeding schedule. Using this feeding schedule, another polymerization is carried out, and the process of adjustment of the parameters described above is repeated.

This process is known as "interative fitting" of data to a curve. After 4 or 5 such iterative fittings, the experimental VP, MAPTAC and ODMA curves will be matched, as shown in FIG. 2 herein.

The matched curves of VP, MAPTAC and ODMA in FIG. 2 will have at least one set of values for $a_1$, $a_2$, $a_3$ and $a_4$ (the last set of the iterative fitting process) for suitable feeding of MAPTAC and ODMA over the entire period of polymerization. One such set is:

| MAPTAC | ODMA |
|---|---|
| $a_1 = 41$ | $a_1 = 56$ |
| $a_2 = 82$ | $a_2 = 90$ |
| $a_3 = 10$ | $a_3 = 10$ |
| $a_4 = 79$ | $a_4 = 67$ |

C. With such schedules available, a homogeneous terpolymer of VP, MAPTAC and ODMA can be prepared as described in Example 2 below.

EXAMPLE 2

Preparation of a Homogeneous Terpolymer of VP, MAPTAC and ODMA

VP (303.6 g), MAPTAC (7.8 g), ODMA (3.i g), and ethanol (1001.0 g) are charged into a 2-liter resin pot equipped with a gas inlet, a liquid inlet, a thermometer and a condenser. The pH of the solution is adjusted to about 7.5 with KOH. Then a stream of nitrogen is introduced which bubbles through the solution during the reaction. The solution is gradually heated to 65° C. Then MAPTAC (63.2 g) and octadecyl methacrylate (ODMA) (51.4 g) are introduced incrementally into the pot with vigorous stirring over a period of 5 hours so that the relative concentrations of the monomeric VP, MAPTA and ODMA monomer remain practically constant throughout the reaction at predetermined levels.

As soon as MAPTAC and ODMA is introduced to the pot, Lupersol 11 (t-butylperoxy pivalate in mineral spirits) catalyst is added. The rate of the addition of the catalyst is such that 2 ml of Lupersol is completely delivered in 4 hours. The solution is held for an additional 3 hours at the 68° C. The product is an alcoholic solution of the homogeneous terpolymer of VP, MAPTAC and ODMA.

180 g of the polymer solution then was transferred to a 2-liter flask and 500 g of distilled water was added. The resulting solution then was stripped under reduced pressure at 40°–50° C. on a rotovap to remove 200 g of solvent (ethanol/water). A clear viscous polymer solution in water was obtained.

The sequence and mode of addition of monomers during the process is summarized in the Table below and the plot in FIG. 2.

TABLE

HOMOGENEOUS POLYMERIZATION OF VP, MAPTAC AND ODMA

| Time (min) | VP (g) | MAPTAC (g) | ODMA (g) | EtOH (g) | Total (g) |
|---|---|---|---|---|---|
| 0 | 303.6 | 7.8 | 3.1 | 1001.0 | 1315.46 |
| 0–30 | 0 | 13.2 | 10.3 | 0.0 | 1338.93 |
| 30–60 | 0 | 11.9 | 10.3 | 0.0 | 1361.12 |
| 60–90 | 0 | 10.0 | 8.6 | 0.0 | 1379.66 |
| 90–120 | 0 | 8.0 | 6.8 | 0.0 | 1394.48 |
| 120–150 | 0 | 6.3 | 5.1 | 0.0 | 1405.88 |
| 150–180 | 0 | 4.7 | 3.7 | 0.0 | 1414.36 |
| 180–210 | 0 | 3.5 | 2.6 | 0.0 | 1420.50 |
| 210–240 | 0 | 2.5 | 1.8 | 0.0 | 1424.86 |
| 240–270 | 0 | 1.8 | 1.2 | 0.0 | 1427.90 |
| 270–300 | 0 | 1.3 | 0.8 | 0.0 | 1430.00 |
| Total | 303.6 | 71.0 | 54.5 | 1001.0 | 1430.00 |
| % Wt | 21.23 | 4.96 | 3.81 | 70.00 | 100.00 |
| % wt (t = 0) | 23.08 | 0.59 | 0.23 | 76.10 | 100.00 |

HAIR CARE PRODUCT

The homogeneous terpolymer of the invention contains a predetermined dominant blend of a hydrophilic part, i.e. VP/MAPTAC, and a small proportion of a hydrophobic monomer, i.e. RMA. This homogeneous terpolymer composition enables the terpolymer to be readily adsorbed onto the negatively charged hair in high amounts as clear films, and to provide both styling and conditioning functions, while still being capable of being readily rinsed or washed-off with water or shampoo after use.

In use in a water-based, rinse-off, hair styling and conditioning composition, the homogeneous terpolymer of the invention comprises about 0.2–20%, preferably 1–10%, and, most preferably, about 2–8%, by weight of the hair care product, the rest being water, and, optionally including an organic solvent such as ethanol, and/or other acceptable adjuvant components such as silicones, surface active agents, viscosity modifiers, dyes, chelating agents, distributing aids, pearlescent aids, opacifiers, perfumes, fatty alcohols, pH adjusting agents, and the like.

The homogeneous terpolymer of the invention finds particular utility in multifunctional hair care products such as water-based, rinse-off hair styling and conditioning products, and in leave-on hair care products such as a mousse, and may be included as a concentrate, or as a gel, and applied as a self-actuated pump hair spray, or in an aerosol product with a propellant. Various actuator and packaging devices known in the art may be used therewith.

While the invention has been described with particular reference to certain embodiments thereof, it will be understood that changes and modifications may be made which are within the skill of the art. Accordingly, it is intended to be bound only by the following claims, in which:

What is claimed is:

1. A homogeneous polymerization process for making clear solutions of a substantially homogeneous terpolymer comprising by weight, (a) 55–99% of a vinyl lactam, (b) 0.5–49% of an organic quaternary ammonium monomer, and (c) 0.5–49% of a hydrophobic monomer, by polymerization of the monomers in a solvent in the presence of a radical initiator, which comprises:

(a) precharging a reactor with a predetermined amount of the vinyl lactam, and solvent, at a suitable polymerization temperature, and (b) introducing the quaternary amino monomer and the hydrophobic monomer incrementally into said reactor in predetermined rates corresponding to the rate of disappearance of the vinyl lactam, over a given period of time.

2. A process according to claim 1 wherein (a) is vinyl pyrrolidone, (b) is a quaternary salt of an amino acrylamide or methacrylamide, an amino acrylate or methacrylate, and (c) is a hydrophobic alkyl acrylate or methacrylate, an alkyl acrylamide or methacrylamide.

3. A process according to claim 1 wherein (a) is vinyl pyrrolidone, (b) is an organic quaternized ammonium methacrylamide, and (c) is a $C_4$–$C_{32}$ alkyl methacrylate.

4. A process according to claim 1 where (a) is vinyl pyrrolidone, (b) is 3-methacrylamidopropyl trimethylammonium chloride, and (c) is octadecyl methacrylate.

5. A process according to claim 1 wherein (b) and (c) are introduced incrementally so that all the monomers can react to form a substantially homogeneous terpolymer whose composition approaches the nominal monomer ratio of the desired terpolymer composition.

6. A process according to claim 1 wherein the solvent is alcohol.

7. A process according to claim 1 wherein said polymerization temperature is about 50°–80° C.

8. A process according to claim 1 which also includes the step of post-heating with additional radical initiator to reduce the residual VP content to <0.1%.

9. A process according to claim 1 wherein (a) is 65–95%, (b) is 0.5–40%, and (c) is 0.5–15%.

10. A process according to claim 1 wherein (a) is 70–90%, (b) is 5–15%, and (c) is 1–10%.

11. A process according to claim 1 wherein (a) is 70–95% vinyl pyrrolidone, (b) is 5–15% 3-methacrylamidopropyl trimethylammonium chloride, and (c) is 1–10% octadecyl methacrylate.

12. A process according to claim 1 wherein the radical initiator is t-butylperoxy pivalate.

13. A process according to claim 1 wherein up to about 15% of each of (b) and (c) is included in the precharge.

* * * * *